US012326425B2

(12) United States Patent
Wrobel (10) Patent No.: US 12,326,425 B2
(45) Date of Patent: Jun. 10, 2025

(54) METHOD FOR EXAMINING MATERIALS USING ACOUSTIC SPECTROSCOPY (71) Applicant: SONOVUM GMBH, Leipzig (DE)

(72) Inventor: Miroslaw Wrobel, Karlstadt (DE)

(73) Assignee: SONOVUM GMBH, Leipzig (DE)

(*) Notice: Subject to any disclaimer, the term of this patent is extended or adjusted under 35 U.S.C. 154(b) by 929 days.

(21) Appl. No.: 17/202,996

(22) Filed: Mar. 16, 2021

(65) Prior Publication Data
US 2021/0325350 A1 Oct. 21, 2021

Related U.S. Application Data (63) Continuation of application No. 15/743,385, filed as application No. PCT/EP2016/063863 on Jun. 16, 2016, now abandoned.

(30) Foreign Application Priority Data

Jul. 17, 2015  (EP) .................................. 15177198
Oct. 26, 2015  (DE) ..................... 10 2015 118 226.2

(51) Int. Cl.
G01N 29/46 (2006.01)
A61B 8/00 (2006.01)
(Continued)

(52) U.S. Cl.
CPC ........... G01N 29/46 (2013.01); A61B 8/0808 (2013.01); A61B 8/4281 (2013.01);
(Continued)

(58) Field of Classification Search
None
See application file for complete search history.

(56) References Cited

U.S. PATENT DOCUMENTS 5,433,112 A   7/1995  Piche et al.
5,492,125 A   2/1996  Kim et al.
(Continued)

FOREIGN PATENT DOCUMENTS

DE   4141123 C1    3/1993
DE   19841154 A1   4/2000
(Continued)

OTHER PUBLICATIONS

Wear KA. The effects of frequency-dependent attenuation and dispersion on sound speed measurements: applications in human trabecular bone. IEEE Trans Ultrason Ferroelectr Freq Control. 2000;47(1):265-73. doi: 10.1109/58.818770. PMID: 18238539; PMCID: PMC9207814. (Year: 2000).*

(Continued)

Primary Examiner — Catherine T. Rastovski
Assistant Examiner — Brian Butler Geiss
(74) Attorney, Agent, or Firm — Quarles & Brady LLP (57) ABSTRACT A device for examining biological and non-biological materials via acoustic spectroscopy includes an ultrasonic transmission device and an ultrasonic reception device for receiving a reflected and/or transmitted ultrasonic reception signal after said signal has passed through the material to be examined. The transmission device transmits ultrasonic transmission signals having different frequencies and the reception device receives corresponding ultrasonic reception signals. Time-of-flight values of the allocated ultrasonic signals can be identified from every signal pair using a first processing device, and the attenuation values of the allocated ultrasonic signal can be identified from every signal pair using a second processing device. For every frequency of the different transmission signals and reception signals, the corresponding identified time-of-flight values and attenuation values can be stored as a results dataset.

17 Claims, 10 Drawing Sheets (51) Int. Cl.
*A61B 8/08* (2006.01)
*G01N 29/024* (2006.01)
*G01N 29/032* (2006.01)
*G01N 29/07* (2006.01)
*G01N 29/11* (2006.01)
*G01N 29/44* (2006.01)

(52) U.S. Cl.
CPC ......... *A61B 8/5207* (2013.01); *G01N 29/024* (2013.01); *G01N 29/032* (2013.01); *G01N 29/07* (2013.01); *G01N 29/11* (2013.01); *G01N 29/44* (2013.01); *G01N 29/4427* (2013.01)

(56) References Cited

U.S. PATENT DOCUMENTS

| | | | |
|---|---|---|---|
| 5,559,292 | A | 9/1996 | Hull et al. |
| 5,635,645 | A | 6/1997 | Ottes et al. |
| 6,109,098 | A | 8/2000 | Dukhin et al. |
| 6,553,366 | B1 | 4/2003 | Miller et al. |
| 2014/0180177 | A1* | 6/2014 | Rothberg ............ A61B 8/4245 601/3 |
| 2015/0041625 | A1 | 2/2015 | Dutton et al. |

FOREIGN PATENT DOCUMENTS

| | | |
|---|---|---|
| DE | 10324990 B3 | 11/2004 |
| DE | 10353132 B3 | 6/2005 |
| DE | 102005005386 B3 | 7/2006 |
| DE | 202007017911 U1 | 3/2008 |
| DE | 102008014300 A1 | 9/2009 |
| EP | 0728443 B1 | 8/2000 |
| WO | 2009083050 A1 | 7/2009 |

OTHER PUBLICATIONS

Gerds et al., A CMOS Time to Digital Converter IC with 2 Level Analog CAM, IEEE Journal of Solid-State Circuits, 1994, 29(9):1068-1076.

Hall et al., Direct Time-to-Digital Converter with Multi-Stop Facility, Nuclear Instruments and Methods, 1977, 140(2):283-287.

Ju, et al., Simultaneous Measurement of Local Longitudinal and Transverse Wave Velocities, Attenuation, Density, and Thickness of Films by Using Point-Focus Ultrasonic Spectroscopy, Journal of Applied Physics, 2012, 112:084910-1 thru 084910-8.

Maatta et al., A High-Precision Time-to-Digital Converter for Pulsed Time-of-Flight Laser Radar Applications, IEEE Transactions on Instrumentation and Measurement, 1998, 47(2):521-536.

Marioli et al., Digital Time-of-Flight Measurement for Ultrasonic Sensors, IEEE Transactions on Instrumentation and Measurement, 1992, 41(1):93-97.

Ronzhin et al., Development of Picoseconds Time of Flight Systems in Meson Test Beam Facility at Fermilab, No. FERMILAB-CONF-10-402-E, Fermi National Accelerator Lab (FNAL), Batavia, IL (United States), 2010.

Svilainis et al., The Time-of-Flight Estimation Accuracy Versus Digitization Parameters, Ultragarsas (Ultrasound), 2008, 63(1):12-17.

Swapp, Time To Digital Converter Resolves Picoseconds in Time Interval Measurements, Motorola 8182 Technical Developments, 1982, vol. 2, p. 53.

Texas Instruments, Ultrasonic TDC Flowmeter Reference Design, TIDU965—May 2015, Copyright 2015 Texas Instruments Incorporated, pp. 1-36.

PCT International Search Report, PCT/EP2016/063863, Sep. 22, 2016.

PCT English Language Translation of the International Preliminary Report on Patentability, PCT/EP2016/063863, Feb. 1, 2018.

* cited by examiner

METHOD FOR EXAMINING MATERIALS USING ACOUSTIC SPECTROSCOPY

This application is a continuation of U.S. patent application Ser. No. 15/743,385 filed on Apr. 10, 2018, which application represents the national stage entry of PCT International Application No. PCT/EP2016/063863 filed on Jun. 16, 2016, which claims the benefit of European Patent Application No. 15177198.7 filed on Jul. 17, 2015 and German Patent Application No. 10 2015 118 226.2 filed on Oct. 26, 2015, the entire contents of which are incorporated herein by reference for all purposes.

The invention relates to a device for examining materials via acoustic spectroscopy according to the preamble of claim 1.

A device for examining liquid or gaseous media via acoustic spectroscopy is known, for example, from DE 103 24 990 B3. In this device, a transmission device for transmitting several transmission signals having different frequencies and a reception device for receiving corresponding reception signals are provided. Using a processing device, the phase shift for each signal pair consisting of the transmission signal and the reception signal can be identified and a value qualifying the examined medium can be derived by means of the phase shift. In the described device, signal packages having different frequencies are transmitted consecutively in direct sequence. The frequencies preferably move in a range from 1 to 15 MHz, with each signal package preferably comprising at least 100 periods. The specific reception signals are captured for each signal package and thus for each frequency step via the reception device and are then directed to a processing device. In the processing device, the phase-shift angle which is arranged between the two signals and which is caused by the passage through the examined medium is identified for each frequency-specific signal pair consisting of the transmission signal and the reception signal. Thus, a plurality of different frequency-specific phase-shift values is ultimately captured via this frequency-specific sampling of the medium, the number of the phase-shift values depending on the number of signal pairs consisting of the transmission signal and the reception signal. In this manner, information on the behavior of the medium can be gathered from a very large frequency range defined via individual frequency steps, said information allowing to draw conclusions on the properties of the examined medium. Due to the frequency-specific sampling of the medium and the corresponding determination of the frequency-related phase angles, the medium can be examined much more specifically since a change of the medium has a different impact on the corresponding frequency-specific signal pair consisting of the transmission signal and the reception signal.

A disadvantage of the device described in DE 103 24 990 B3 is that it is based upon the evaluation of the values of the phase-shift which is caused by the passage of the transmission signal through the material to be examined and is documented via the reception signal. For the evaluation of the phase shift between the transmission signal and the reception signal can lead to undesired losses of information by which the evaluation result is significantly falsified. These losses of information are caused by the fact that the value of the phase shift is limited to a value range between 0° and 360°. Should, however, the phase shift between the transmission signal and the reception signal be greater than 360°, the method described in said document yields a phase-shift value which cannot be clearly allocated. Should the phase shift between the transmission signal and the reception signal be 400°, for example, the evaluation device described in said document yields a phase-shift value of 40°. The evaluation results derived therefrom are thus crucially falsified and unusable since the evaluation yields results which are equivalent to a phase shift of 40° and not to a phase shift of 400° (=360°+40°).

In order to solve this problem, in which results cannot be clearly allocated when evaluating the phase shift between a transmission signal and a reception signal, document DE 198 41 154 A1 proposes generating transmission signals having different frequencies. In this context, the different frequencies serve as a type of nonius when assessing the phase shifts. Thus it is possible to clearly allocate the measured phase-shift values to the actual phase shift between the transmission signal and the reception signal. However, this method has the disadvantage that the sound waves in the medium to be examined are transmitted with different speeds of sound depending on the corresponding transmission frequency, these different transmission speeds possibly leading to crucial measurement errors in the medium to be examined. The dependence of the speed of propagation of the transmission signal on the corresponding transmission frequency is described by the Kramers-Kronig relation. In this respect, the measuring method according to DE 198 41 154 A1 has proven to be unsuitable since the measurement errors cannot be taken into account due to the inconsistent speed of propagation of the sound waves in dependence on the corresponding transmission frequency.

The principles of acoustic spectroscopy, which form the basis of the device according to the invention, are described, though by no means exclusively, in the following reference books, for example:

Reference book 1: *Molekularakustik* [Molecular Acoustics], Werner Schaaffs, published by Springer Verlag, 1963 (ISBN-10:3642491413, ISBN-13:978-3642491412)

Reference book 2: *Molecular Acoustics/Molekularakustik*, K.-H. Hellwege, A. M. Hellwege, W. Schaaffs, published by Springer Verlag, 1967 (ISBN-10:3540038973, ISBN-13:978-3540038979)

Reference book 3: *Molecular Acoustics*, A. J. Matheson, John Wiley & Sons Publishers, 1971 (ISBN-10: 1861561857, ISBN-13:978-1861561855)

Starting from this generic device as a basis, a device for non-invasive examination of materials via acoustic spectroscopy is to be proposed. When examining body tissue in particular, though not exclusively, for diagnostic purposes, there is often the problem that body tissue cannot be readily removed for examination, so that only noninvasive examination methods can be employed. If, for example, the human brain is to be examined, removing body tissue is not possible in almost all cases due to the incalculable side effects associated with opening the human skull.

The object of the invention at hand is to propose a device for noninvasively examining materials, in particular body tissue, via acoustic spectroscopy, the sources of error described above being able to be precluded by means of said device.

This object is attained by a device according to the teachings of claim 1.

Advantageous embodiments of the invention are the subject matter of the dependent claims.

The device according to the invention generically comprises an ultrasonic transmission device for transmitting ultrasonic transmission signals and an ultrasonic reception device for receiving the reflected or transmitted ultrasonic reception signals. The transmission device as well as the reception device is suitable for transmitting and receiving, respectively, ultrasonic signals having different frequencies.

In contrast to the teachings from DE 103 24 990 B3, however, the phase shift is not determined for every signal pair consisting of the transmission signal and the reception signal when evaluating the signals. Instead, the time of flight of the allocated ultrasonic signal is identified from every signal pair consisting of the transmission signal and the reception signal in a first processing device. Simultaneously, the attenuation of the allocated ultrasonic signal, when said signal passes through the material to be examined, is identified from every signal pair consisting of the transmission signal and the reception signal in a second processing device. In other words, this means that by using the device according to the invention a data pair having the corresponding time of flight and the corresponding attenuation can be identified from every signal pair consisting of the transmission signal and the reception signal of a specific frequency as a result and can be stored for the corresponding frequency in a storage device. According to the invention, it is not required for this purpose to capture all data for describing a pair of signals consisting of the transmission signal and the reception signal. It is not required, for example, to know the phase of the transmission signal since the phase of the transmission signal is not required for identifying the time of flight and the attenuation of the transmission signal when said signal passes through the material to be examined. Thus, only those data for describing the transmission signal and the reception signal have to be captured which are necessary for identifying the time of flight and the attenuation.

For examinations on test materials, e.g. human body tissue, when subjecting said materials to ultrasonic signals and when identifying the time of flight on the one hand and the attenuation on the other hand for every individual signal pair consisting of the transmission signal and the reception signal, have demonstrated that changes in the material are significantly depicted in the results data pairs from the time of flight and the attenuation. The conventional acoustic spectroscopy, in which the signal attenuation is to be measured, is thus expanded according to the invention to the effect that for every frequency not only the specific frequency-dependent attenuation (ATN) but also the specific frequency-dependent time of flight (ToF) is determined. By measuring the time of flight, the dispersivity of the examined material can be determined. The combination of measuring the attenuation and the dispersivity of the examined material allows a highly differentiated characterization of the examined material.

Examinations on a plurality of test subjects have shown, for example, that changes in tissue of the human brain are accompanied by changes in the dispersive character of the brain tissue, said changes in the dispersive character being able to be identified using the device according to the invention. In this manner, the risk of stroke for a patient can be captured as a consequence of changes in the brain tissue and can be quantitatively assessed. Changes in the brain tissue also occur with Alzheimer's disease and Parkinson's disease, said changes in the brain tissue being accompanied by significant changes in the time of flight and the attenuation when said tissue is subjected to ultrasonic signals, and being able to be identified using the device according to the invention. Thus the device according to the invention provides an appliance by means of which pathological changes in body tissue can be identified by means of noninvasive acoustic spectroscopy and can be quantitatively assessed.

When using the device according to the invention for noninvasively examining materials, very large results datasets are accumulated since a results dataset having the corresponding time of flight and the corresponding attenuation is determined and stored for each frequency and the allocated signal pair consisting of the transmission and the reception signal. If a large number of examinations are carried out and if this data is to be evaluated by comparing the results datasets with data from a previously set-up results databank, problems regarding processing can easily arise due to the large data volume. It is therefore particularly advantageous if a reduced results dataset can be derived from the identified results dataset in a data reduction device, said reduced results dataset characteristically depicting the identified results dataset and comprising a small data volume. The data processing can be significantly accelerated when evaluating the results data via this data reduction of the results data.

In which manner the data reduction device reduces the results datasets is generally arbitrary. According to a first variation, the corresponding maximal time of flight and minimal time of flight as well as the corresponding maximal attenuation and minimal attenuation is determined in a results dataset which contains all transmission frequencies and all signal pairs consisting of the transmission signal and the reception signal for examining a material. These two maximal values and minimal values form a reduced results dataset. This data reduction can be assumed as being characteristic of the original dataset since the rectangular data quadrant spanned by the two maximal values and the two minimal values comprises all other results data.

The data can be reduced even further if not only the results data of one results dataset but also the results data of several results datasets are summarized in the data reduction device. If, for example, a plurality of persons has been examined, the results data from the results datasets of all male test subjects on the one hand and the results data from the results datasets of all female test subjects on the other hand can be summarized, for example. The reduced results datasets then represent, on the one hand, the results data of the male test subjects and, on the other hand, the results data of the female test subjects. Likewise, the results datasets can also be summarized for different age groups, for example. Which groups are summarized when reducing the results data is generally arbitrary and merely depends on the corresponding desired examination result. In order to summarize the results data from several identified results data, the corresponding maximal time-of-flight value and the minimal time-of-flight value and the corresponding maximal attenuation value and the minimal attenuation value can be determined by means of the data reduction device in all results datasets which represent a group. The two maximal values and the two minimal values span a results data space which comprises and represents the results data from all of the summarized results datasets.

Another possibility for reducing data consists in determining at least one quantile of the time-of-flight values in an identified results dataset as well as at least one quantile of the attenuation values in this results dataset in the data reduction device. These quantiles are then stored as a reduced results dataset. In the scope of the invention, a quantile is to be understood as being a statistical threshold value in the amount of the time-of-flight values or the amount of the attenuation values of one or more results datasets.

In which manner the results datasets identified by means of the device according to the invention or rather the reduced results datasets derived therefrom are used is generally arbitrary. It is particularly advantageous if an evaluation which yields a value qualifying the material, e.g. body tissue, can be carried out by means of the device. A specific examination and the derivation of values qualifying the examined material can be easily achieved via the frequency-specific sampling of the medium and the corresponding determination of the attenuation on the one hand and of the time of flight on the other hand, since a change in the medium significantly affects the corresponding results datasets.

When evaluating the results datasets or when evaluating the reduced results datasets, the following exemplary methods exist for the evaluation, the classification and the modulation:

Multiple Linear Regression (MLR)
Principle Component Regression (PCR)
Partial Least Square Regression (PLSR)
L-shaped Partial Least Square Regression (L-PLSR)
Support Vector Machine Regression (SVM-R)

In which manner the qualifying value for describing the examined material is derived from the results datasets or from the reduced results datasets in the evaluation device is generally arbitrary. It is particularly advantageous if the derivation is carried out in the manner of a pattern comparison in which the results datasets are compared to comparative results datasets from a databank. In this context, the comparative results datasets represent measurements of comparative materials having known properties. In this context, the comparative material can be body tissue of patients having known illnesses, e.g. Alzheimer's disease, Parkinson's disease or hypertension. It is also conceivable to representationally render the comparative results datasets when measuring cell tissue having special markings in the cells.

This type of pattern comparison leads to highly differentiated examination results since the results datasets identified using the device according to the invention provide a type of fingerprint for each material depending on its specific properties, said results data pairs having the time of flight and the attenuation forming a data pattern for the different frequencies, said data pattern being able to characterize the examined material and its properties. Each change in the examined material is accompanied by a change of this fingerprint, which is represented by the results dataset. If the fingerprint represented by the results dataset is compared to the fingerprints of the comparative results datasets in the databank, a highly differentiated conclusion on the corresponding examined material can be drawn via this pattern comparison method. Such pattern comparisons very often require results datasets being classified, for which the following methods may be applied:

Principle Component Analysis (PCA)
Partial Least Square Analysis (PLSA)
Linear Discriminate Analysis (LDA)
Support Vector Machine Classification (SVM-C)
Partial Least Square Discriminant Analysis (PLS-DA)
Soft Independent Modelling of Class Analogy (SIMCA)

In contrast to the previous examination methods, the phase shift is no longer determined by means of the device according to the invention but instead the time of flight of the ultrasonic signal itself is determined. In order to be able to determine the properties of the examined material using an adequate resolution, it is particularly advantageous if the time of flight can be determined with a resolution of at least 100 picoseconds in the first processing device. Preferably, the time of flight should be able to be determined with a resolution of at least 10 picoseconds.

Which time measuring device is provided in the first processing device for determining the time of flight is generally arbitrary. In order to yield resolutions, in particular in the range of below 10 picoseconds, when measuring the time of flight, it is particularly advantageous if so-called time-to-digital converters are used for this purpose. These time-to-digital converters are electronic component groups which can measure temporal intervals in the range of lesser than 100 picoseconds and can convert them to a digital version. The measurement of time is based upon the known time of flight of an electric signal through the component groups of the time-to-digital converter. The time of flight is then determined by how many of the electronic circuits having a known time of flight are passed through between transmitting the transmission signal on the one hand and receiving the reception signal on the other hand. This number of passages through electronic component groups having a known time of flight is then counted, the measured time of flight corresponding to the multiplication of the known time of flight of an individual circuit by the number of passages.

In order to be able to correctly evaluate the results datasets, it is of great importance that the time-of-flight value and the attenuation value are identified by means of the identical signal pair consisting of the transmission signal and the reception signal. For the smallest of changes in the properties of the examined material, such as the change in blood pressure in a body tissue, can lead to the results data being falsified if the attenuation and the time of flight are determined consecutively and not by means of the identical signal pair consisting of the transmission signal and the reception signal. In order to enable this, the device according to the invention contains a signal splitter, by means of which a correspondingly received ultrasonic reception signal can be directed to the first processing device for determining the time of flight and to the second processing device for determining the attenuation identically for parallel processing.

Which type of material is examined using the device according to the invention is generally arbitrary. The device is particularly suitable for noninvasively examining body tissue. In this case, the body tissue of a body part to be examined is subjected to the ultrasonic transmission signals, and the ultrasonic reception signals are recorded after passing through the body tissue. The device according to the invention can be used with great advantage when examining the human brain since so far examinations on the human brain, in particular molecular or cellular examinations, could otherwise not be carried out at all or with only very poor conclusive results. Since opening the human skull for examining brain tissue is not possible in almost all cases due to the considerable side effects, brain tissue can so far only be examined by means of imaging methods, e.g. magnetic resonance imaging or computer tomography, as a general rule. However, these imaging methods generally do not enable drawing differentiated diagnostic conclusions on most kinds of pathologies in the brain. In particular, Alzheimer's disease and Parkinson's disease can be diagnosed by means of the imaging methods only at a stage at which an effective therapy is no longer possible in most cases. In order to be able to examine the brain tissue by means of the device according to the invention, the ultrasonic transmission device or the ultrasonic reception device should be suitable for being temporarily and/or permanently arranged on the outer side of the patient's scalp. When the ultrasonic transmission device or ultrasonic reception device is arranged on the scalp in this way, a doctor is commonly not required since arranging the transmission device and the reception device can be carried out by correspondingly trained care staff or even by laymen.

Which type of ultrasonic waves is utilized for examination by means of the device according to the invention is generally arbitrary. Longitudinal ultrasonic waves in the lower MHz range are particularly suitable.

It is further conceivable that the ultrasonic transmission signals having different frequencies can be consecutively transmitted from the ultrasonic transmission device individually or as groups.

Alternatively, the ultrasonic transmission signal for the different frequencies can be modulated onto a shared carrier signal and can be transmitted therefrom by means of the ultrasonic transmission device. It is also possible to add the ultrasonic transmission signals having different frequencies in the ultrasonic transmission device to a shared carrier signal as a superposition and transmit them together.

According to the invention, transmission signals having different frequencies are generated by the transmission device in order to identify a signal pair consisting of the transmission signal and the reception signal for each of these frequencies and to evaluate said signal pair consisting of the transmission signal and the reception signal for characterization of the examined material. Besides the change in frequency, it can also be advantageous to transmit ultrasonic transmission signals each having different amplitudes using the transmission device. By this means, the data can be evaluated in an even more differentiated way.

In the following, the invention is further described in an exemplary manner by means of an embodiment schematically illustrated in the drawings.

In the figures.

Figure 1:
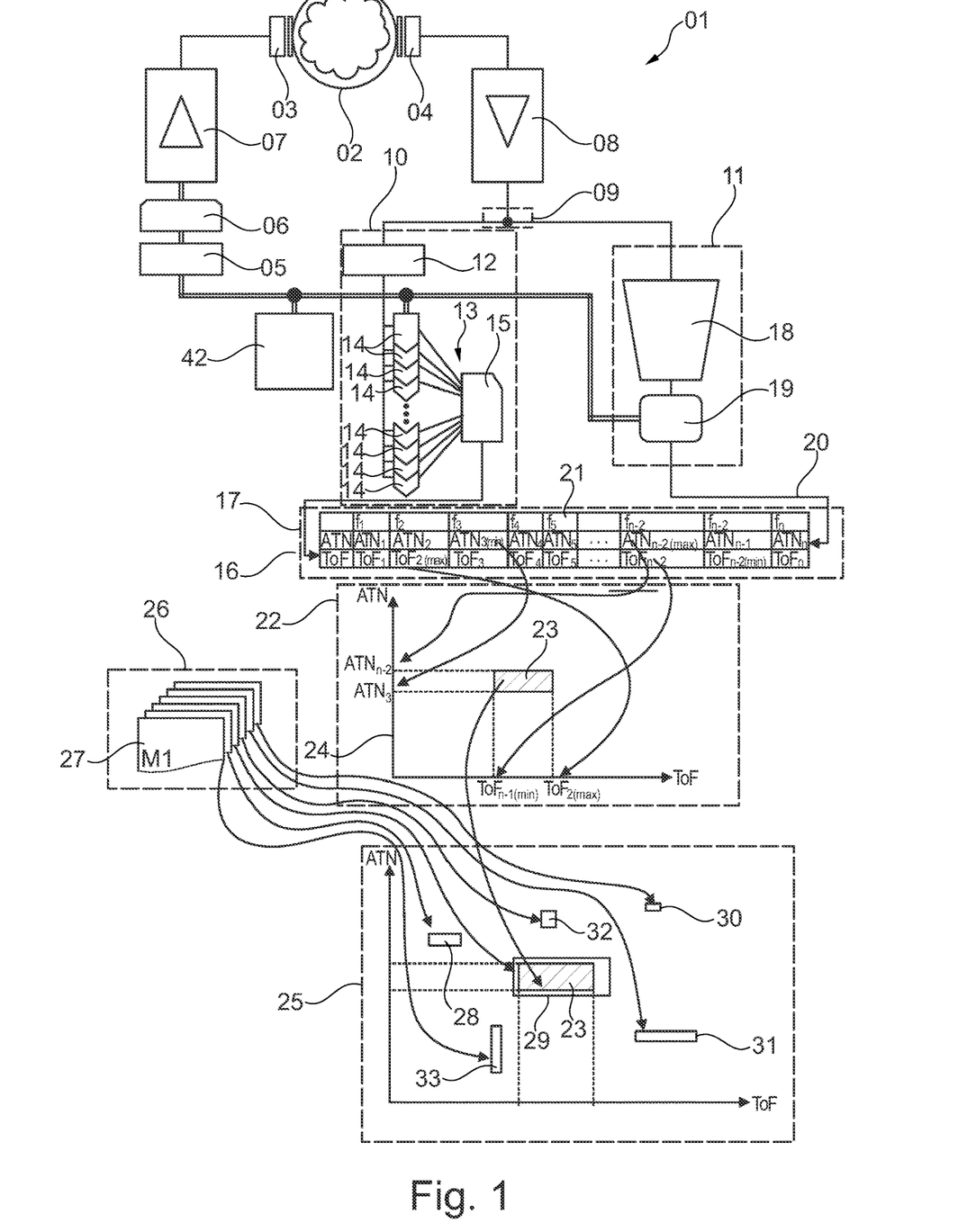
FIG. 1 illustrates a device according to the invention having different functional modules in a schematic sketch.

In a schematic sketch, FIG. 1 illustrates the general setup of a device 01 according to the invention as can be utilized for noninvasively examining a material 02, such as a brain, such as a skull, via methods of acoustic spectroscopy. The device 01 comprises, on the one hand, an ultrasonic transmission device 03 and an ultrasonic reception device 04. The device 01 further comprises a signal preparation module 05 for generating the ultrasonic signals to be emitted from the ultrasonic transmission device 03, a signal generator 06, and a signal amplifier 07.

After directly passing through or indirectly passing through (reflection) the body tissue 02, the ultrasonic signals are captured at the ultrasonic reception device 04 and are amplified by means of a signal amplifier 08. The amplified reception signals are subsequently divided in a signal splitter 09 and are distributed to a first processing device 10 and a second processing device 11 for parallel processing. The first processing device 10 serves for determining the times of flight which the ultrasonic signal requires for passing through the body tissue 02 for the individually set frequencies. After passing through a signal processing module 12, the reception signal arrives in a time-to-digital converter 13 by means of which the time of flight of the ultrasonic signal, i.e. the time between the emission from the ultrasonic transmission device 03 and the reception of the ultrasonic signal at the ultrasonic reception device 04, can be measured. The function of the time-to-digital converter 13 is based upon the fact that the time of flight of an electrical signal passing through a plurality of electronic circuits 14 contained in the time-to-digital converter 13 is known.

In order to measure the time of flight, the trigger signal of the ultrasonic transmission signal is also directed to the time-to-digital converter 13 simultaneously with the emission from the ultrasonic transmission device 03 in order to start the time-measuring process. The trigger signal of the ultrasonic transmission signal then passes through the consecutively arranged circuits 14 in the time-to-digital converter 13. Each passage through an electronic circuit 14, which corresponds to a predetermined time of flight, is added up by a counter 15 for this purpose. As soon as the reception signal is directed to the electronic circuits 14, the counter 15 stops and multiplies the number of added passages by the known time of flight of the individual electronic circuits 14. From this, the overall time of flight 16 is yielded for a signal pair consisting of the transmission signal and the reception signal. A time of flight 16 is yielded for every transmission frequency and is stored with the corresponding allocated transmission frequency in a storage device 17.

Parallel thereto, the signal attenuation of the ultrasonic transmission signal is determined in the second processing device 11 when the signal passes through the body tissue 02. For this purpose, a signal processing module 18 is provided in the second processing device 11, said signal processing module 18 processing the signal and identifying the amplitude of the ultrasonic reception signal. Subsequently, the amplitude of the ultrasonic reception signal is compared to the amplitude of the ultrasonic transmission signal in an evaluation module 19. Via this comparison, the corresponding attenuation 20 can be determined in the second processing device 11 for each frequency of a signal pair consisting of the transmission signal and the reception signal and can be stored in the storage device 17.

When carrying out an examination on body tissue 02, predefined signal paths having different transmission frequencies are defined by a control 42 and are subsequently emitted by the ultrasonic transmission device 03. For each individual frequency, the time of flight 16 and the attenuation value 20 are determined by evaluating the signal pair consisting of the transmission signal and the reception signal generated from the frequency and are stored in the storage device 17. At the end of the measuring process on the body tissue 02, a results dataset 21 is stored in the storage device 17. The results dataset 21 contains the corresponding time of flight 16 and the corresponding attenuation value 20 for each of the frequencies $f_1$ to $f_n$ so that the results dataset 21 represents a fingerprint of the material properties of the body tissue 02 identified via acoustic spectroscopy.

A data reduction device 22 is arranged downstream of the storage device, the functionality of said data reduction device 22 being described in the following by means of the schematic sketch in FIG. 2.

Figure 2:
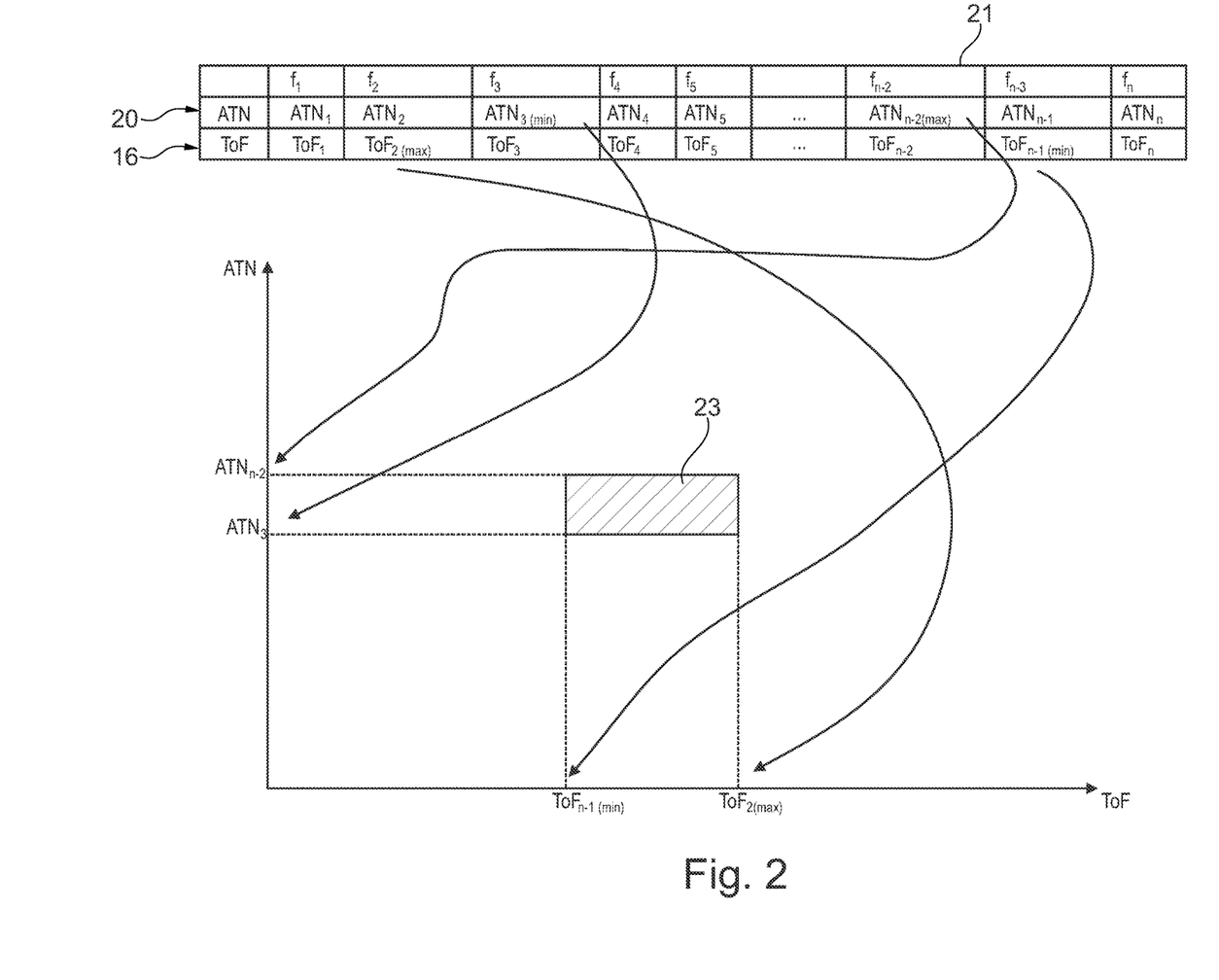
FIG. 2 illustrates a schematic sketch for describing the mode of operation of a first data reduction device.

FIG. 2 represents an exemplary results dataset 21 in which the corresponding times of flight (ToF) and the corresponding attenuation values (ATN) are stored for each transmission frequency $f_1$ to $f_n$. The results dataset 21 can definitely contain a large amount of data if, for example, the corresponding time of flight and the corresponding attenuation have been determined on a body tissue 02 for several hundred frequencies. In order to facilitate evaluating the results dataset 21, a data reduction can be carried out in the data reduction device 22 as follows: the maximal values and the minimal values are determined from the times of flight 16 stored in the results dataset 21 and the stored attenuation values 20, respectively. In the example illustrated in FIG. 2, the attenuation value $ATN_3$ represents the minimum attenuation value and the attenuation value $ATN_{n-2}$ represents the maximum attenuation value. Furthermore, the time-of-flight value $ToF_2$ represents the maximum time-of-flight and the time-of-flight value $ToF_{n-1}$ represents the minimum time-of-flight.

These two minimal values and the two maximal values for the time of flight and the attenuation, respectively, constitute a reduced results dataset 23, said results dataset 23 being represented by a rectangle when entered in a coordinate system 24. Since the reduced results dataset 23 has been derived from the different attenuation values and time-of-flight values via the two minimal values and the two maximal values, it can be concluded that the rectangle 23 representing the reduced results dataset comprises all other data of the results dataset 21 with its inner surface and thus represents all of the data of the results dataset 21.

As can be seen in FIG. 1, an evaluation device 25 is arranged downstream of the data reduction device 22, said evaluation device 25 interacting with a databank 26 when evaluating the reduced results datasets 23. For this purpose, a plurality of comparative results datasets 27 is stored in the databank 26, said plurality of comparative results datasets 27 having been determined via measurements on comparative body parts having known properties. The mode of operation of the evaluation device 25 in interaction with the databank 26 is to be further described by means of the schematic sketch in FIG. 3 and FIG. 4.

Figure 3:
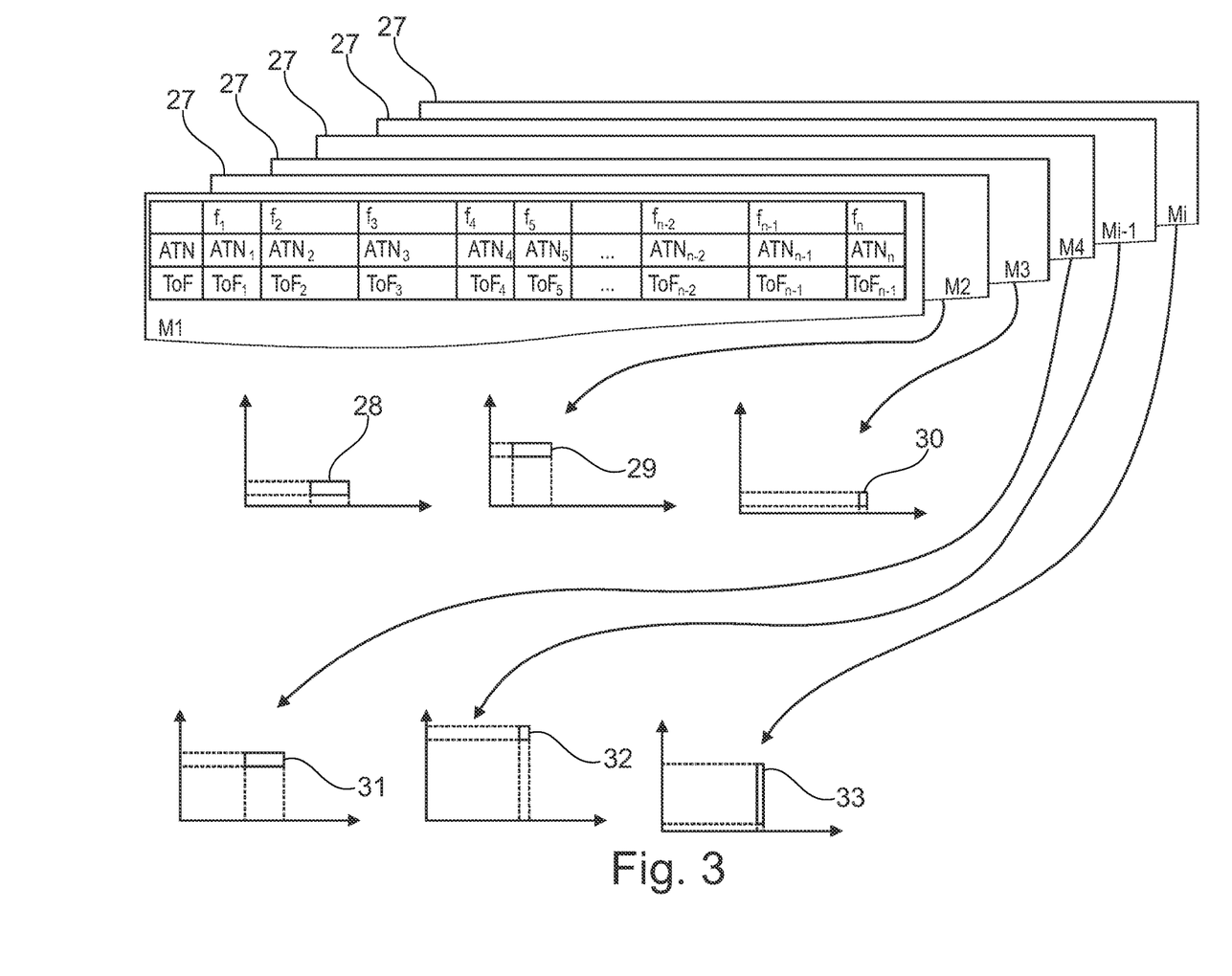
FIG. 3 illustrates a schematic sketch for describing the set up of a databank having comparative results datasets.

FIG. 3 first of all illustrates the databank 26 having the different comparative results datasets 27. Each comparative results dataset 27 has been identified via acoustic spectroscopy on a comparative body part having known properties.

In order to enable the pattern comparison of the reduced results dataset 21, which has been determined via measurements on the body tissue 02, with the data of the comparative datasets 27 in the databank 26, a data reduction is carried out for each of the comparative results datasets, as described in FIG. 2 above. In other words, this means that a reduced results dataset 28, 29, 30, 31, 32 and 33 is determined for each comparative results dataset, said reduced results dataset 28, 29, 30, 31, 32 and 33 each being represented by a rectangle in the coordinate system of time of flight and attenuation.

As can be seen in FIG. 1, a pattern comparison of the reduced results dataset 23, which represents the body tissue 02, with the reduced comparative results datasets 28 to 30 is carried out in the evaluation device 25. As illustrated in an exemplary manner in FIG. 1, the reduced results dataset 23 of the body tissue 02 shows the closest matches with the reduced comparative results dataset 29. By this, the body tissue 02 can be qualified in the evaluation device 25 as having properties comparable to the properties of the comparative body part which is represented by the reduced results dataset 29. In other words, this means that, after carrying out the pattern comparison, the evaluation device 25 can indicate that the body tissue 02 significantly matches the body tissue represented by the reduced comparative results dataset 29.

Figure 4:
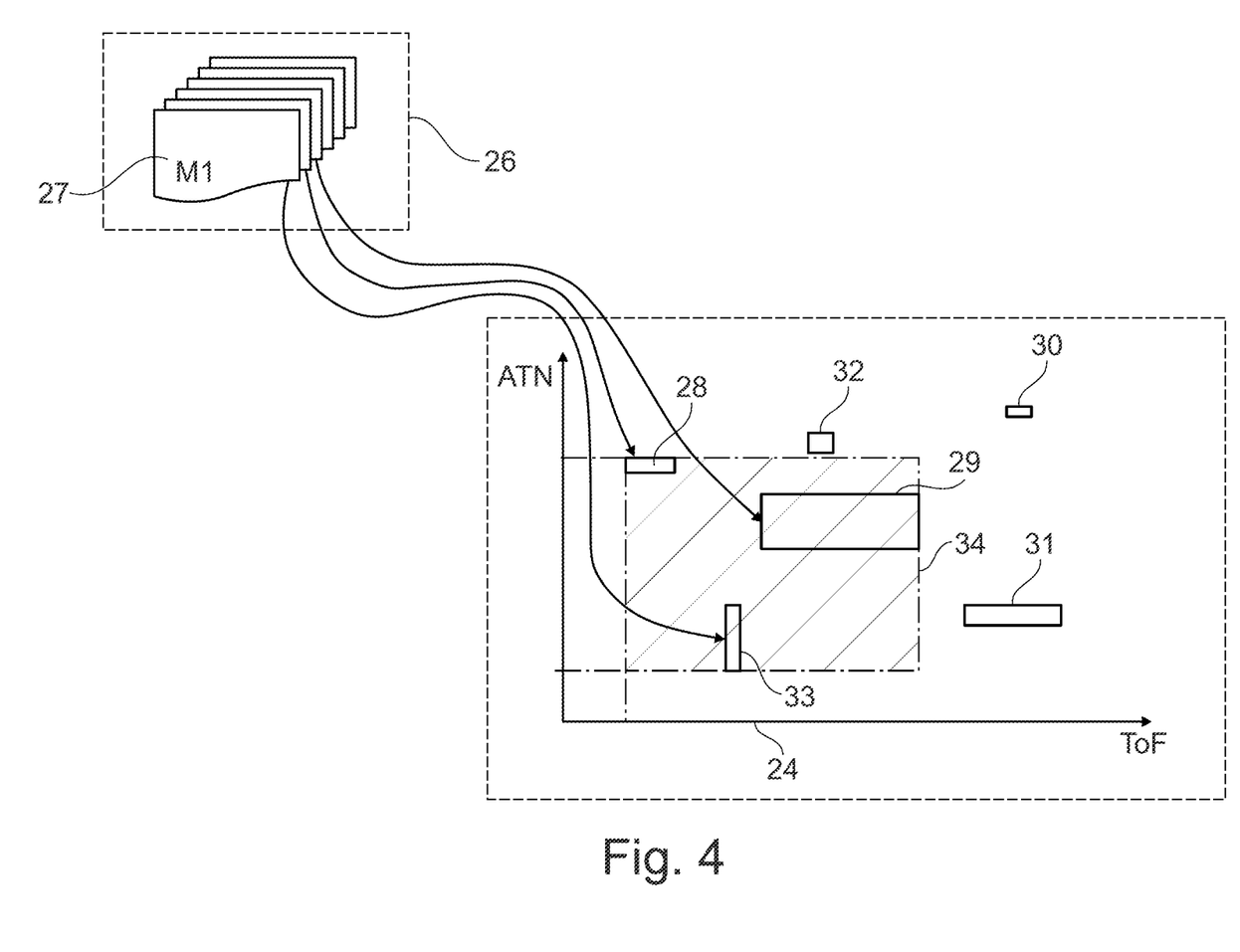
FIG. 4 illustrates a schematic sketch for describing the mode of operation of an evaluation unit of the device according to FIG. 1 when using a databank according to FIG. 3.

FIG. 4 serves for describing another variation of reducing data in the device according to the invention. This is to be described in an exemplary manner by means of the data reduction of the data in the databank 26 having the comparative datasets 27. As previously described, each results dataset 27 of the databank 26 can be depicted on a reduced results dataset which is represented as a rectangle in the coordinate system of time of flight and attenuation. If one continues to assume, for example, that the first three results datasets 27 in the databank 26 are allocated to patients belonging to a category having specific properties, such as patients suffering from hypertension, all other results datasets in the databank 26 are then allocated to patients who do not suffer from hypertension. If an additionally reduced results dataset 34 is to be identified for patients belonging to the category of patients suffering from hypertension, this may be achieved in that the two minimal values and maximal values for the time of flight and the attenuation, respectively, are identified from the corresponding results datasets 27 of the three results datasets representing the respective category. This category of patients suffering from hypertension can then be represented by the reduced results dataset 34.

FIG. 5 to FIG. 11 illustrate the signal paths 35 to 41 in a time domain, said signal paths 35 to 41 being able to be used as ultrasonic transmission signals on the device 01, for example. Parallel thereto, the corresponding frequency of the signal paths 35 to 41 is indicated in Hertz.

Figure 5:
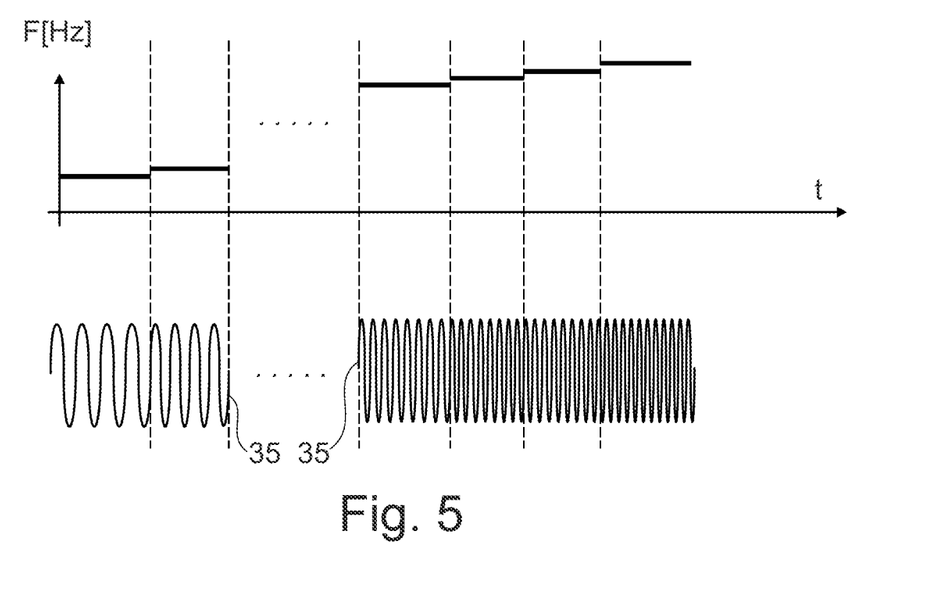
FIG. 5 illustrates the signal path and the signal frequencies of an ultrasonic transmission signal.

As with signal path 35, the ultrasonic transmission signal can comprise sections having an increasing frequency in each instance, the difference in frequency being equidistant between the individual sections.

Figure 6:
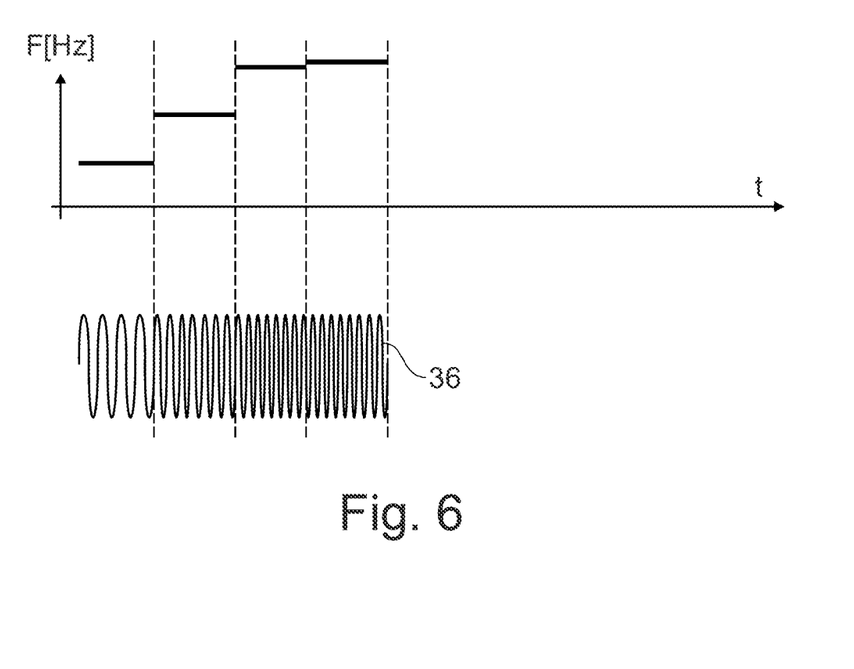
FIG. 6 illustrates the signal path and the signal frequencies of a second ultrasonic transmission signal.

As can be seen in FIG. 6, the difference in frequency between the individual frequency sections of the signal path 36 can be chosen to not be equidistant.

Figure 7:
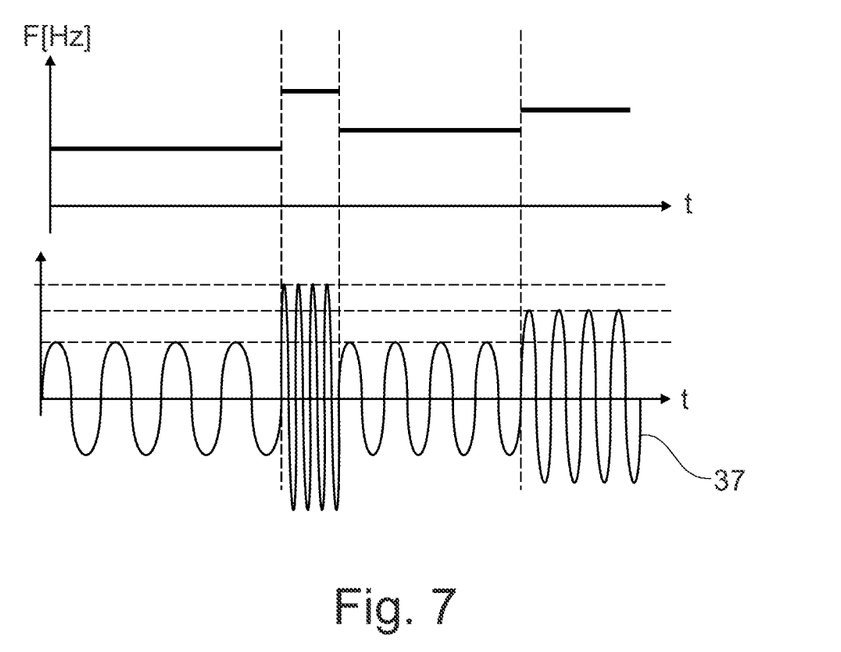
FIG. 7 illustrates the signal path and the signal frequencies of a third ultrasonic transmission signal.

As can be seen in FIG. 7, the signal path 37 can also be varied with regard to the amplitude of the ultrasonic transmission signal in dependence on the corresponding transmission frequency.

Figure 8:
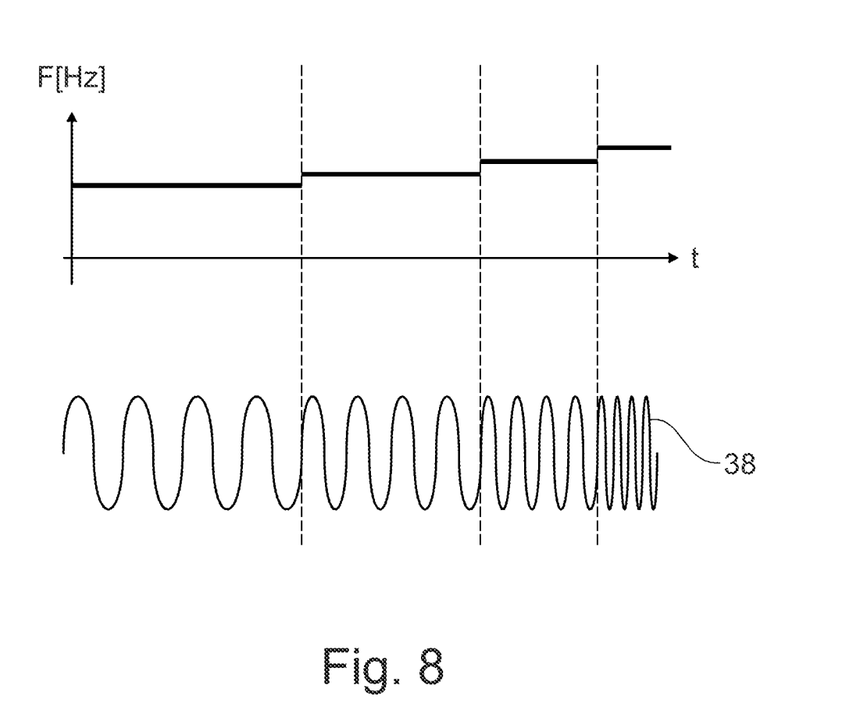
FIG. 8 illustrates the signal path and the signal frequencies of a fourth ultrasonic transmission signal.

FIG. 8 illustrates a signal path 38 of the ultrasonic transmission signal having an equidistantly increasing transmission frequency in each instance, the duration of the individual transmission sections becoming increasingly shorter so that a constant number of passages is available in each section.

Figure 9:
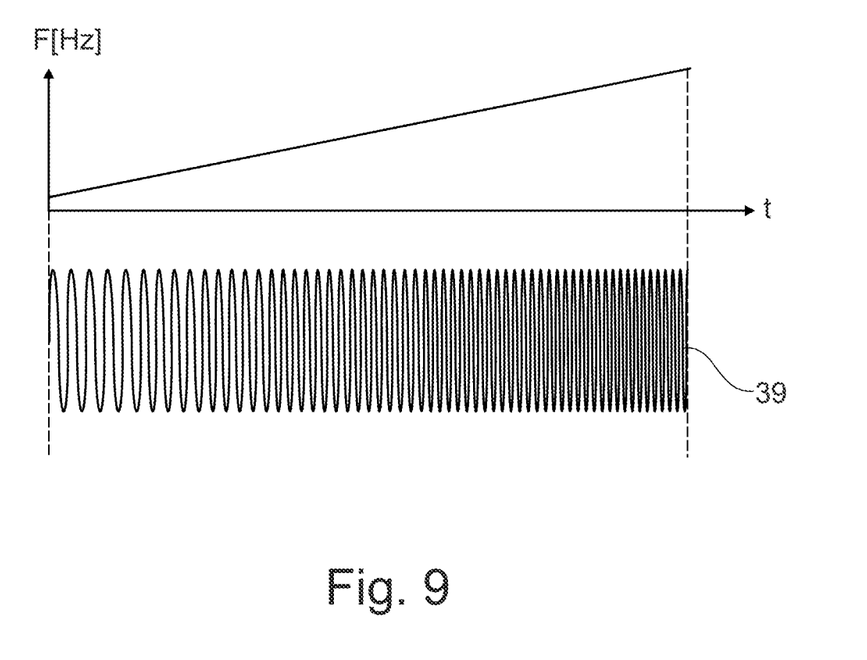
FIG. 9 illustrates the signal path and the signal frequencies of a fifth ultrasonic transmission signal.

As is described in FIG. 9, the signal path 39 of the ultrasonic transmission signal can also be emitted using a continuously increasing transmission frequency, such as a linear FM-modulated transmission signal.

Figure 10:
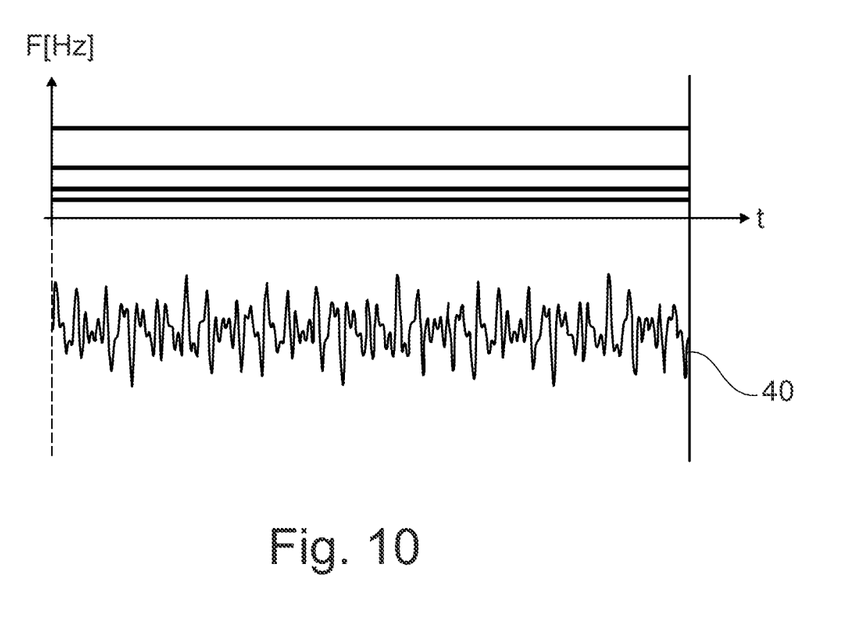
FIG. 10 illustrates the signal path and the signal frequencies of a sixth ultrasonic transmission signal.

FIG. 10 illustrates a transmission signal path 40 having four transmission frequencies superposing each other.

Figure 11:
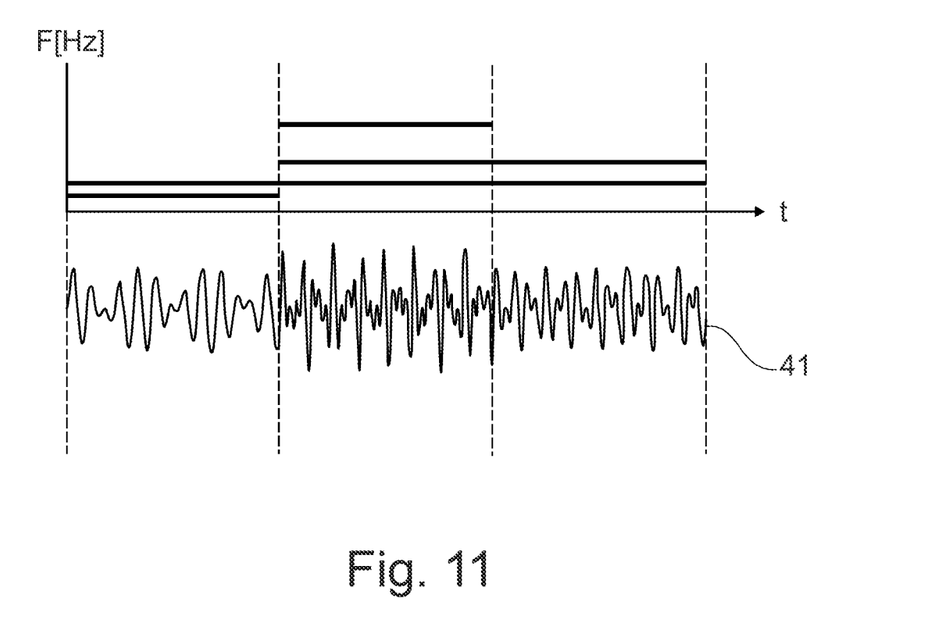
FIG. 11 illustrates the signal path and the signal frequencies of a seventh ultrasonic transmission signal.

The signal path 41 of the ultrasonic transmission signal is generated by adding various transmission frequencies onto a shared transmission signal (superposition), individual frequencies either being added or being able to be omitted in the different sections.

The invention claimed is:

1. A method for examining biological and non-biological materials via acoustic spectroscopy, said method comprising the following steps:
   transmitting a plurality of ultrasonic transmission signals, each of the plurality of transmission signals being transmitted at a different frequency from the others of the plurality of transmission signals;
   receiving a corresponding plurality of reflected or transmitted ultrasonic reception signals after the signals passed through a material to be examined;
   determining a time of flight and directly measuring frequency dependent time-of-flight values for each of the plurality of transmission signals and the corresponding reception signal;
   identifying frequency-dependent attenuation values for each of the plurality of transmission signals and the corresponding reception signal; and
   storing the time of flight values and the attenuation values for each frequency in a results dataset.

2. The method according to claim 1, further comprising the step of deriving a reduced results dataset from the results dataset, said reduced results dataset having a smaller data volume than the results dataset.

3. The method according to claim 2, further comprising the step of determining the maximal time-of-flight value and the minimal time-of-flight value in the results data set and the maximal attenuation value and the minimal attenuation value in the results data set and storing the maximum time-of-flight value, the minimal time-of-flight value, the maximal attenuation value, and the minimal attenuation value as the reduced results dataset.

4. The method according to claim 2, further comprising the step of determining the maximal time-of-flight value, the minimal time-of-flight value, the maximal attenuation value, and the minimal attenuation value in said several results datasets, and storing the maximal time-of-flight value, minimal time of flight value, maximal attenuation value, and minimal attenuation value as the reduced results dataset.

5. The method according to claim 2, further comprising the step of determining at least one quantile of the time-of-flight values in the results dataset and at least one quantile of the attenuation values in the results dataset, and storing the quantiles as the reduced results dataset.

6. The method according to claim 1, further comprising the step of deriving at least one value qualifying the material from the results dataset or the reduced results dataset.

7. The method according to claim 6, wherein the qualifying value is derived on the basis of a pattern comparison of the results dataset or reduced results datasets with comparative results datasets stored in a databank, said comparative results datasets having been determined by measuring comparative materials having known properties.

8. The method according to claim 1, further comprising the step of identifying the time-of-flight with a resolution of at least 10 picoseconds.

9. The method according to claim 1, further comprising the step of parallel processing a received ultrasonic reception signal.

10. The method according to claim 1, further comprising the step of generating the longitudinal ultrasonic waves in the range between 1 and 15 MHz.

11. The method according to claim 1, further comprising the step of individually transmitting the plurality of ultrasonic transmission signals having different frequencies one after the other.

12. The method according to claim 1, further comprising the step of modulating ultrasonic transmission signals having different frequencies on a shared carrier signal in the ultrasonic transmission device and transmitting together.

13. The method according to claim 1, further comprising the step of transmitting each of the plurality of ultrasonic transmission signals at a different amplitude from the others of the plurality of ultrasonic transmission signals.

14. The method according to claim 2, further comprising the step of deriving at least one value qualifying the material from the results dataset or the reduced results dataset.

15. The method of claim 1, wherein the material to be examined is body tissue.

16. A method for examining biological and non-biological materials via acoustic spectroscopy, said method comprising the following steps:
   transmitting a plurality of ultrasonic transmission signals, each of the plurality of transmission signals being transmitted at a different frequency from the others of the plurality of transmission signals;
   receiving a corresponding plurality of reflected or transmitted ultrasonic reception signals after the signals passed through a material to be examined;
   determining a time of flight and directly measuring frequency dependent time-of-flight values for each of the plurality of transmission signals and the corresponding reception signal;
   measuring frequency-dependent attenuation values for each of the plurality of transmission signals and the corresponding reception signal; and
   storing the time of flight values and the attenuation values for each frequency in a results dataset.

17. A method for examining biological and non-biological materials via acoustic spectroscopy, said method comprising the following steps:
   transmitting a plurality of ultrasonic transmission signals, each of the plurality of transmission signals being transmitted at a different frequency from the others of the plurality of transmission signals;
   receiving a corresponding plurality of reflected or transmitted ultrasonic reception signals after the signals passed through a material to be examined;
   parallel processing the corresponding plurality of reflected or transmitted ultrasonic reception signals by splitting the corresponding plurality of reflected or transmitted ultrasonic reception signals and directing the corresponding plurality of reflected or transmitted ultrasonic reception signals to a first processing device and a second processing device;
   determining a time of flight and directly measuring frequency dependent time-of-flight values for each of the plurality of transmission signals and the corresponding reception signal by the first processing device and identifying frequency-dependent attenuation values for each of the plurality of transmission signals and the corresponding reception signal by the second processing device; and
   storing the time of flight values and the attenuation values for each frequency in a results dataset.

* * * * *